(12) United States Patent  (10) Patent No.: US 9,097,647 B2
Baba  (45) Date of Patent: Aug. 4, 2015

(54) METHOD FOR USING POLARIZATION GATING TO MEASURE A SCATTERING SAMPLE

(71) Applicant: UT-Battelle, LLC, Oak Ridge, TN (US)

(72) Inventor: Justin S. Baba, Knoxville, TN (US)

(73) Assignee: UT-Battelle, LLC, Oak Ridge, TN (US)

( * ) Notice: Subject to any disclaimer, the term of this patent is extended or adjusted under 35 U.S.C. 154(b) by 100 days.

(21) Appl. No.: 13/962,826

(22) Filed: Aug. 8, 2013

(65) Prior Publication Data

US 2014/0043609 A1  Feb. 13, 2014

Related U.S. Application Data

(60) Provisional application No. 61/680,774, filed on Aug. 8, 2012.

(51) Int. Cl.
   *G01N 21/21* (2006.01)
   *G01N 21/51* (2006.01)

(52) U.S. Cl.
   CPC ............... *G01N 21/21* (2013.01); *G01N 21/51* (2013.01)

(58) Field of Classification Search
   USPC ............. 356/33, 364–369; 250/341.1, 341.3, 250/225
   See application file for complete search history.

(56) References Cited

U.S. PATENT DOCUMENTS

| | | | |
|---|---|---|---|
| 4,203,670 A * | 5/1980 | Bromberg | 356/367 |
| 4,699,514 A * | 10/1987 | Schmidt et al. | 356/367 |
| 4,841,157 A | 6/1989 | Downing, Jr. | |
| 4,850,710 A * | 7/1989 | Mochida et al. | 356/367 |
| 4,953,980 A * | 9/1990 | DeVolk et al. | 356/338 |
| 5,241,368 A | 8/1993 | Ponstingl et al. | |
| 5,311,290 A * | 5/1994 | Olson et al. | 356/634 |
| 5,350,922 A | 9/1994 | Bartz | |
| 5,408,321 A * | 4/1995 | Paulson, Jr. | 356/366 |
| 5,453,832 A | 9/1995 | Joyce | |
| 5,719,399 A * | 2/1998 | Alfano et al. | 250/341.3 |
| 5,722,406 A | 3/1998 | Papaioannou | |
| D402,768 S | 12/1998 | Paoli et al. | |
| 6,166,807 A * | 12/2000 | Kawamura et al. | 356/364 |
| 6,327,488 B1 | 12/2001 | Van Der Mark et al. | |
| 6,327,489 B1 | 12/2001 | Hoogenraad et al. | |
| 6,415,172 B1 | 7/2002 | Painchaud et al. | |
| 6,594,510 B2 * | 7/2003 | Madarasz et al. | 600/310 |
| 6,864,985 B1 | 3/2005 | Tanzer | |
| 6,982,790 B1 | 1/2006 | Gershenson | |
| 6,985,227 B2 * | 1/2006 | Wang | 356/364 |
| 7,002,685 B2 * | 2/2006 | Wang | 356/364 |

(Continued)

OTHER PUBLICATIONS

"The Melles Griot 13AMP005 Wideband Detector Amplifier User's Guide; 9060-98001", 11pp. (date unknown).

(Continued)

*Primary Examiner* — Sang Nguyen
(74) *Attorney, Agent, or Firm* — Klarquist Sparkman, LLP

(57) ABSTRACT

Described herein are systems, devices, and methods facilitating optical characterization of scattering samples. A polarized optical beam can be directed to pass through a sample to be tested. The optical beam exiting the sample can then be analyzed to determine its degree of polarization, from which other properties of the sample can be determined. In some cases, an apparatus can include a source of an optical beam, an input polarizer, a sample, an output polarizer, and a photodetector. In some cases, a signal from a photodetector can be processed through attenuation, variable offset, and variable gain.

14 Claims, 12 Drawing Sheets

(56) References Cited

U.S. PATENT DOCUMENTS

| | | |
|---|---|---|
| 7,084,976 B2 * | 8/2006 | Morokawa et al. ........... 356/364 |
| 7,142,299 B2 | 11/2006 | Tokhtuev et al. |
| 7,239,392 B2 * | 7/2007 | Chism, II ..................... 356/369 |
| 7,400,407 B2 | 7/2008 | Ng et al. |
| D596,926 S | 7/2009 | Venkateraman et al. |
| 7,663,751 B1 | 2/2010 | Mitchell |
| 7,986,411 B2 | 7/2011 | Ziegler et al. |
| 8,004,676 B1 * | 8/2011 | Prasad et al. ................. 356/369 |
| 8,213,016 B2 | 7/2012 | Muller et al. |
| 2002/0159061 A1 | 10/2002 | Ottens et al. |
| 2007/0008530 A1 * | 1/2007 | Gibbs et al. ................... 356/368 |
| 2009/0225317 A1 * | 9/2009 | Tanaka .......................... 356/369 |
| 2009/0244516 A1 * | 10/2009 | Mehendale et al. ............ 356/33 |
| 2010/0104149 A1 | 4/2010 | Nielsen et al. |
| 2011/0273710 A1 | 11/2011 | Dong et al. |
| 2012/0022794 A1 | 1/2012 | Andelic et al. |
| 2012/0090654 A1 | 4/2012 | Bewley, Jr. |

OTHER PUBLICATIONS

Melles Griot "Wide-Bandwidth Amplifier; 39.10—Photodiodes, Integrating Spheres, and Amplifiers," 1 pp. (date unknown).

* cited by examiner

METHOD FOR USING POLARIZATION GATING TO MEASURE A SCATTERING SAMPLE

CROSS REFERENCE TO RELATED APPLICATION

This application claims the benefit of U.S. Provisional Application No. 61/680,774, filed Aug. 8, 2012, which is incorporated herein by reference in its entirety.

ACKNOWLEDGMENT OF GOVERNMENT SUPPORT

This invention was made with government support under Contract No. DE-AC05-00OR22725 awarded by the U.S. Department of Energy. The government has certain rights in the invention.

FIELD

The disclosure pertains to optical characterization of scattering samples.

BACKGROUND

Systems for measuring properties such as concentration or turbidity of a wide range of samples such as dispersions, gas mixtures, solutions, suspensions, colloids, aerosols, foams, emulsions, gels, and/or sols, are useful in many fields. For example, environmental quality standards can be based on turbidity or a concentration of suspended particulates in a sample, as measured by a nephelometer or other turbidimeter. Accurate measurements of the concentration of samples in food, pharmaceutical, and biotechnology industries can allow improvement in yields and quality control and assurance in production processes. Conventional methods tend to be overly complex and often require careful calibration and signal analysis. Improved methods for making these and other measurements are desirable.

SUMMARY

Described herein are systems, devices, and methods facilitating optical characterization of scattering samples. In some embodiments, an optical system comprises an input polarizer situated to receive an optical beam, produce a polarized input optical beam, and direct the polarized input beam to a sample, an output polarizer situated to receive the polarized input optical beam from the sample and form an output optical beam, a photodetector situated to receive the output optical beam, and a photodetector processor coupled to the photodetector and configured to provide an output value based on a comparison of a photosignal from the photodetector and a predetermined reference value, wherein the output value is associated with a degree of polarization of the output optical beam.

In some embodiments, the photodetector processor can be configured to indicate a photosignal transition about the reference value based on a rotation of the output polarizer, can be configured so that the reference value is a zero value, can be configured to provide an estimate of a degree of polarization based on an output polarizer angle of rotation, and can be configured to indicate a zero crossing. In some embodiments, the input polarizer and the output polarizer are linear polarizers, while in others embodiments, the input polarizer and the output polarizer are elliptical or circular polarizers.

In some embodiments, the photosignal from the photodetector is a photocurrent, and the photodetector processor is configured to combine an offset current with the photocurrent to form an output current and the reference value is associated with the output current. The photodetector processor can be configured such that the output transitions from a minimum value to a maximum value at output polarizer rotation angles within 1.0 degree of the rotation angle associated with the reference value. In some cases, the reference value can be midway between values associated with maximum and minimum optical intensity.

In some embodiments, a method comprises selecting a reference value of a photocurrent, coupling a photodetector so as to direct a photocurrent and an offset current associated with the reference value of the photocurrent to an amplifier, selecting an amplifier gain so that the amplifier is saturated at photosignal values that differ by less than about 10% from the reference value, based on an angle of rotation between a polarizer and an analyzer situated to assess a polarization modulation associated with a sample, adjusting the photosignal so as to be substantially equal to the offset current, and determining a degree of polarization from the angle of rotation. In some embodiments, the method can further comprise estimating a turbidity of a sample based on the degree of polarization. In some embodiments, the method can further comprise delivering a polarized optical beam to a sample, wherein the photocurrent is based on a portion of the polarized optical beam received from the sample.

In some embodiments, the output polarizer can be a linear polarizer, the photocurrent and the offset current can be coupled to the amplifier as a sum current, the amplifier gain can be selected so that the amplifier is saturated at photosignal values that differ by less than about 1% from the reference value, the amplifier can be a transimpedance amplifier having a variable transimpedance gain, and the amplifier output can be configured to be zero for a photocurrent that is equal to the offset current.

In some embodiments, an apparatus can comprise a polarizer configured to receive an optical beam and direct a polarized optical beam to a sample, a rotatable analyzer configured to receive the polarized optical beam from the sample, and an amplifier configured to receive a photocurrent based on the received optical beam, and provide an amplifier output that transitions between a maximum output value and a minimum output value at a photocurrent magnitude corresponding to a reference value. In some embodiments, the apparatus can further comprise a processor configured to establish an estimate of a degree of polarization of the received optical beam based on an orientation of the analyzer associated with a photocurrent magnitude corresponding to the reference value.

In some embodiments, the polarizer and analyzer can be linear polarizers, and the minimum output value of the amplifier is a negative value and the maximum value is a positive value, wherein the minimum and maximum values are associated with the plus and minus rails of an amplifier power supply. In some embodiments, the processor can be configured to estimate sample turbidity based on the established degree of polarization. In some embodiments, the apparatus can further comprise a source configured to provide the optical beam. In some embodiments, the polarizer and analyzer are static and employ a mechanically or electro-optically rotatable half wave plate.

The foregoing and other objects, features, and advantages of the invention will become more apparent from the following detailed description, which proceeds with reference to the accompanying figures.

DETAILED DESCRIPTION

Figure 1:
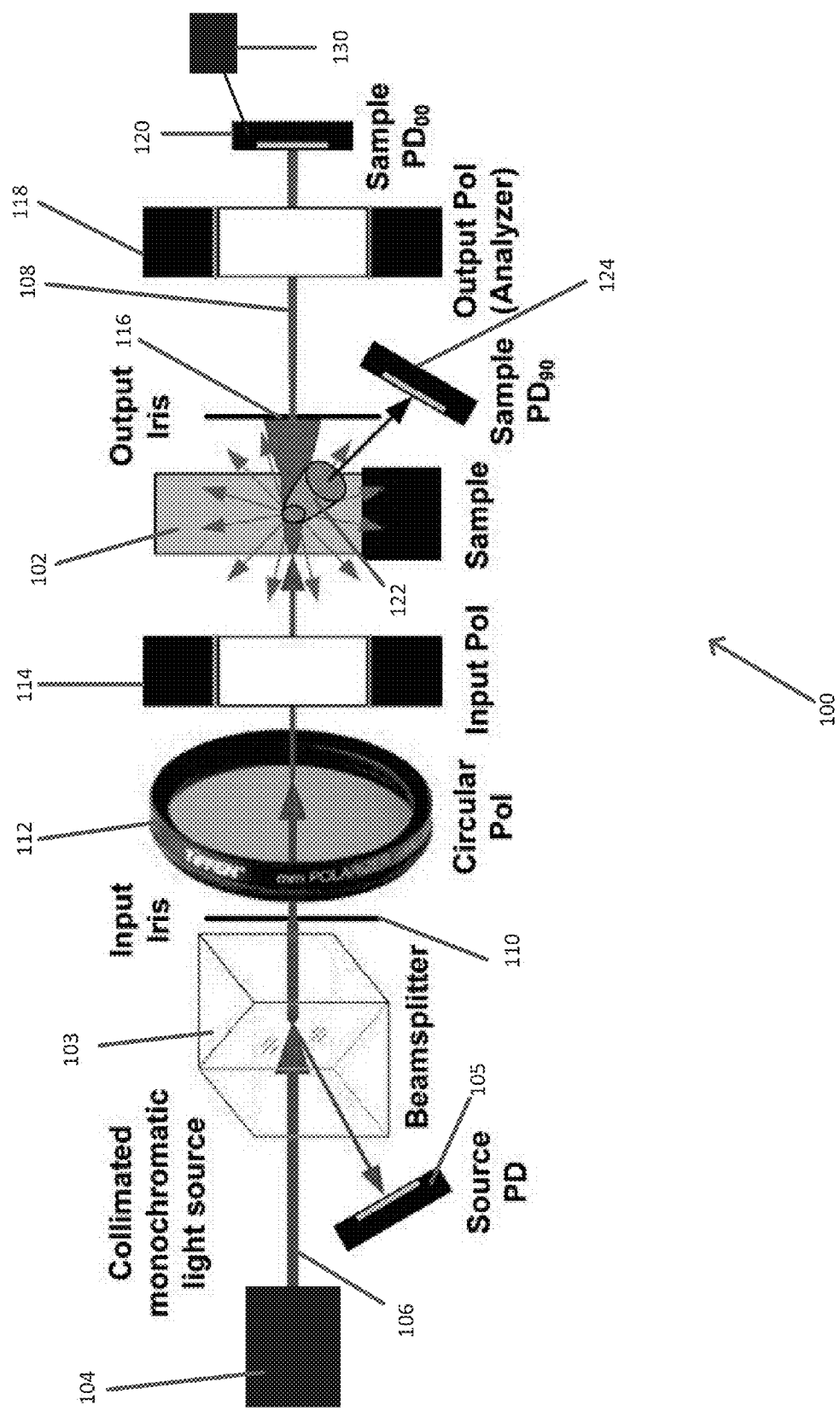
FIG. 1 is a schematic diagram illustrating a representative optical system configured for sample measurements based on a degree of polarization.

As used in this application and in the claims, the singular forms "a," "an," and "the" include the plural forms unless the context clearly dictates otherwise. Additionally, the term "includes" means "comprises." Further, the term "coupled" does not exclude the presence of intermediate elements between the coupled items.

The systems, apparatus, and methods described herein should not be construed as limiting in any way. Instead, the present disclosure is directed toward all novel and non-obvious features and aspects of the various disclosed embodiments, alone and in various combinations and sub-combinations with one another. The disclosed systems, methods, and apparatus are not limited to any specific aspect or feature or combinations thereof, nor do the disclosed systems, methods, and apparatus require that any one or more specific advantages be present or problems be solved. Any theories of operation are to facilitate explanation, but the disclosed systems, methods, and apparatus are not limited to such theories of operation.

Although the operations of some of the disclosed methods are described in a particular, sequential order for convenient presentation, it should be understood that this manner of description encompasses rearrangement, unless a particular ordering is required by specific language set forth below. For example, operations described sequentially may in some cases be rearranged or performed concurrently. Moreover, for the sake of simplicity, the attached figures may not show the various ways in which the disclosed systems, methods, and apparatus can be used in conjunction with other systems, methods, and apparatus. Additionally, the description sometimes uses terms like "produce" and "provide" to describe the disclosed methods. These terms are high-level abstractions of the actual operations that are performed. The actual operations that correspond to these terms will vary depending on the particular implementation and are readily discernible by one of ordinary skill in the art.

In some examples, values, procedures, or apparatus' are referred to as "lowest", "best", "minimum," or the like. It will be appreciated that such descriptions are intended to indicate that a selection among many used functional alternatives can be made, and such selections need not be better, smaller, or otherwise preferable to other selections.

Described herein are embodiments of devices, methods and systems that use optical polarizers to measure properties of scattering and other samples. The disclosed methods and systems can be used to determine a degree of polarization of an optical beam exiting a scattering sample, and the measured degree of polarization can be related to sample characteristics such as turbidity or concentration. In some embodiments, a series of optical elements is aligned along an axis referred to herein as an optical axis. While the optical axis is generally described herein as a continuous linear axis for clarity, the optical axis can be bent, folded, curved or otherwise arranged based on arrangements of optical elements such as mirror, lenses, prisms, diffraction gratings, or other reflective or refractive optical elements.

As used herein, optical element refers to reflective, refractive, diffractive, or other optical elements that attenuate, shape, or direct optical radiation as well as optical radiation sources and optical detectors. As used herein, "optical beam" refers to electromagnetic radiation propagating along an axis and having a cross-section that is associated with a beam diameter, and typically in a wavelength range between about 100 nm and 10 µm, 200 nm and 2 µm, 300 nm and 1.5 µm, or 400 nm to 700 nm. Such an optical beam can be converging or diverging in one or more directions. For example, an optical beam propagating along a z-axis of a rectilinear coordinate system can have different beam divergences angles and beam radii with respect an x-axis and a y-axis. In some examples, optical beams are referred to as collimated such that a beam diameter varies by less than about a factor of between 0.5 and 2 over a selected propagation distance.

In typical examples, a first element of a series of optical elements is an optical beam source configured to produce an optical beam that propagates along the optical axis. Any of various suitable sources of light can be used. For example, the source can be configured to produce an optical beam in a predetermined spectral range, such as an infrared beam, visible beam, ultraviolet beam, X-ray beam, or any other suitable spectral range or combination of spectral ranges. In some embodiments, the source can be configured to emit collimated light. For example, the source can be a laser, or an incoherent source such as an arc lamp can be provided with beam shaping optical system so as to produce an optical beam. In some examples, the source is configured to provide a monochromatic or narrow band optical beam. For example, an optical beam can be provided by a laser, or a broadband optical source can produce radiation that is directed to an optical filter, diffraction grating, or other wavelength selective optical element so as to produce an optical beam having a suitable spectral bandwidth.

In some examples, a last element of a series of optical elements is a photodetector situated to receive an optical beam modulated by a specimen. Typical photodetectors are responsive to incident optical power and produce corresponding electrical signals such as photocurrents or photovoltages. Such electrical signals can be coupled to additional processing circuitry such as amplifiers (including transimpedance amplifiers), buffers, filters, or analog to digital convertors (ADCs). Digitized representations of such electrical signals can be further processed based on computer-executable instructions supplied to a processing system such as a personal computer, tablet, or a dedicated processor. By appropriate configuration of optical elements along an optical axis between the source and the photodetector, measurements of optical beam power incident on the photodetector can be used to quantify optical properties of the sample. Photodetectors such as photodiodes are convenient.

The sample to be measured can be any absorptive or non-absorptive material. For example, the sample can comprise any of various dispersions, gas mixtures, solutions, suspensions, colloids, aerosols, foams, emulsions, gels, and/or sols. In some specific applications, the sample can comprise a sample of environmental material, a sample of biological material, or a sample of material for use in the food, pharmaceutical, or biotechnology industries. Specific examples include syrups, molasses, lotions, sunscreen, and nondairy creamer. The systems, devices, and methods disclosed herein can be used to evaluate optical properties of such samples, which can be useful in and of themselves, and/or can be related to properties of the sample, such as turbidity, haziness, and concentration.

FIGS. 1-4 illustrate several exemplary embodiments of suitable optical systems. With reference to FIG. 1, a system 100 is configured for measurement of optical properties of a scattering sample 102, and comprises an optical beam source 104 that produces an optical beam 106 that is directed along an axis 108. The optical beam 106 is typically a collimated, monochromatic or narrow band optical beam. The system 100 can further comprise, along an optical axis 108 from the optical beam source 104, an input iris 110, a circular polarizer 112, an input polarizer 114, an output iris 116, an output polarizer 118, and an analyzer photodiode 120. As used herein, an input polarizer and an output polarizer configured for evaluation of a beam state of polarization (SOP) are sometimes referred to simply as a polarizer and an analyzer, respectively. The analyzer photodiode is coupled to an amplifier 130 that is configured to permit determination of a critical angle from which specimen characteristics can be determined as discussed in detail below.

As shown in FIG. 1, the optical beam 106 is directed to a beam splitter 103 that transmits a portion of the beam along the optical axis 108, and reflects a portion to a source photodiode 105. An output of the source photodiode 105 can be used for monitoring or compensation of optical power fluctuations in the optical beam 106. The circular polarizer 112 is generally situated so that at least a portion of the optical beam 106 is transmitting in a single SOP by the input polarizer 114. In typical examples, the input polarizer 114 is a linear polarizer that produces a linearly polarized beam that is directed to the sample 102. The output polarizer is typically a linear polarizer, and at least one of the input polarizer 114 and the output polarizer 118 can be rotated about the optical axis 108 by a rotation angle $\Theta$, but typically only the output polarizer 118 is situated on a rotational stage so as to be rotatable. In some alternative embodiments, an input polarizer and an output polarizer can be static, and the system can include a mechanically or electro-optically rotatable half wave plate which can rotate the polarization state of the optical beam.

A portion 122 of a scattered beam from the sample 102 can be directed to a photodiode 124. In some examples, scattered optical power is measured with the photodiode 124 with the polarizers 114, 118 rotated at 90 degrees with respect to each other ($\Theta = 90$) to permit measurement of attenuation, in conjunction with power measurements based on one or more optical powers detected by the photodetector 120.

The optical beam exiting the sample 102 can have both a polarized component and an unpolarized component, depending on the optical properties of the sample 102. The polarized component typically has the same SOP as the optical beam entering the sample (other SOPs are possible if sample is birefringent) and continues along the optical axis 108. In typical examples, the polarized component is linearly polarized as determined by the polarizer 114, while the unpolarized component corresponds to a scattered portion of the optical beam 108. Thus, the optical radiation exiting the sample 102 can be partially polarized, with a degree of polarization P. The incident power on the photodiode 120 can be represented as the sum of two components: a component attributable to the unpolarized portion of the beam exiting the sample 102 and a component attributable to a polarized beam portion exiting the sample 102. By rotationally displacing the output polarizer 118 with respect to the input polarizer 114 and measuring corresponding changes to beam power at the photodiode 120, information can be obtained regarding the degree of polarization of the beam exiting the sample, and thus optical characteristics of the sample 102.

Figure 2:
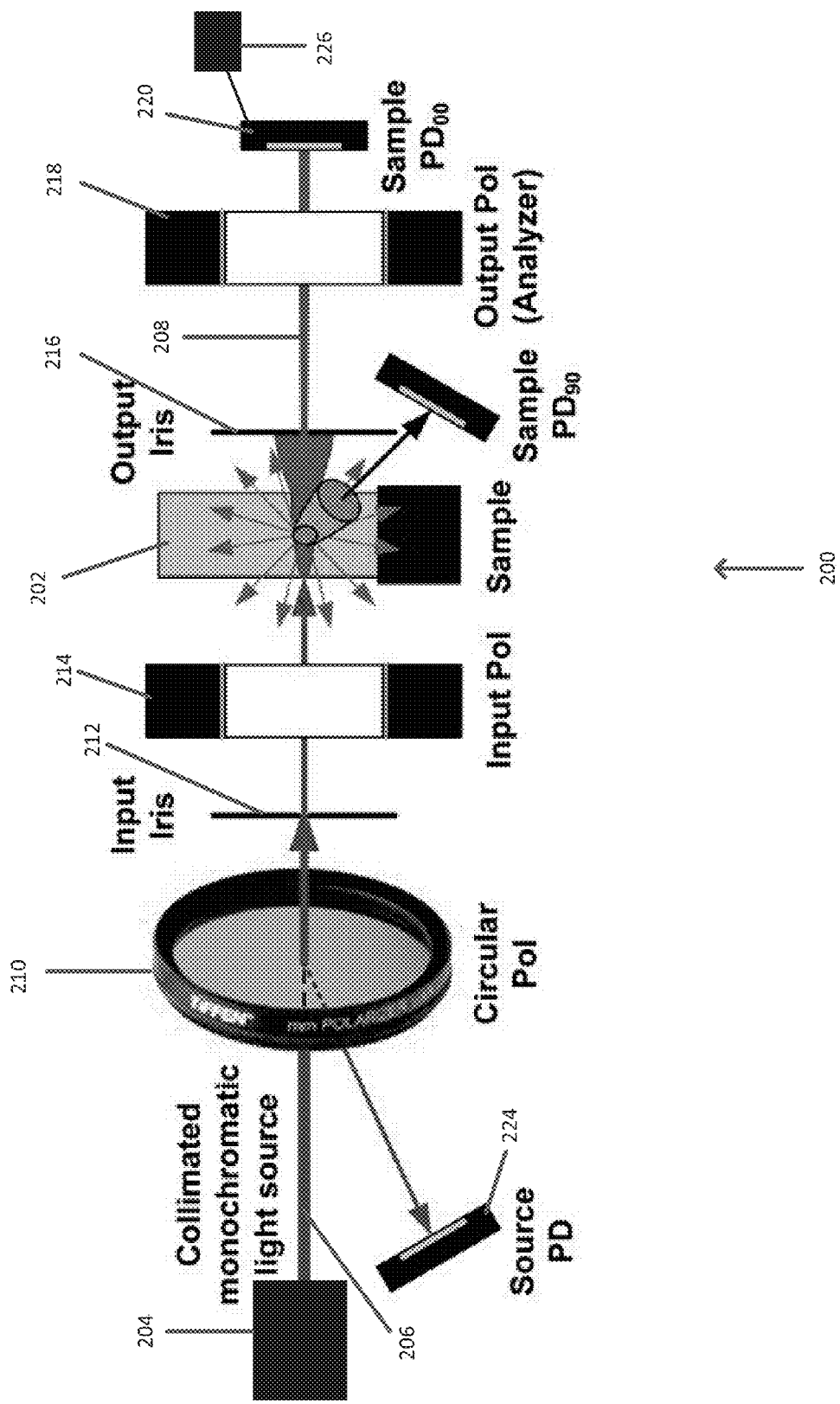
FIG. 2 illustrates a second embodiment of an optical system.

Referring to FIG. 2, a representative system 200 configured to measure optical properties of a scattering sample 202 comprises a source 204 that produces a collimated, monochromatic optical beam 206 that propagates along an optical axis 208. The system 200 can further comprise a circular polarizer 210, an input iris 212, an input polarizer 214, an output iris 216, an output polarizer 218, and a photodiode 220, situated along the axis from the source 204 to the analyzer photodiode 220. A source photodiode 224 is situated to receive a reflected beam portion from the circular polarizer 210, and the analyzer photodiode 220 is coupled to a critical angle detector 226.

Figure 3:
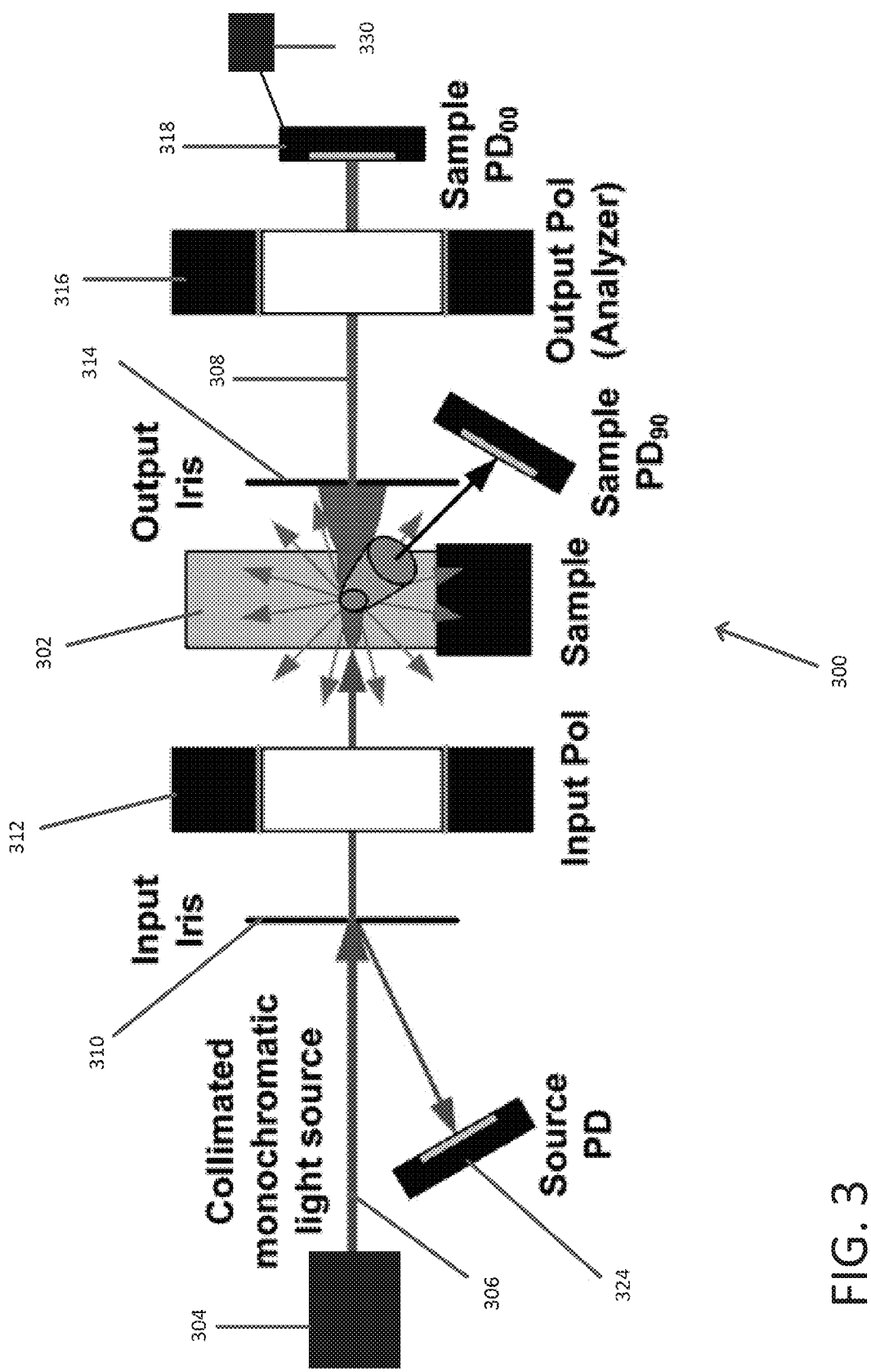
FIG. 3 shows a third embodiment of an optical system.

In another example shown in FIG. 3, a system 300 configured for assessment of a scattering sample 302 comprises a source 304 of an optical beam 306 that is directed along an optical axis 308. The system 300 can further comprise an input iris 310, an input polarizer 312, an output iris 314, an output polarizer 316, and a photodiode 318. The photodiode 318 is coupled to a critical angle processor 330, and a source photodiode 324 is coupled to receive a beam portion from the input iris 310.

Figure 4:
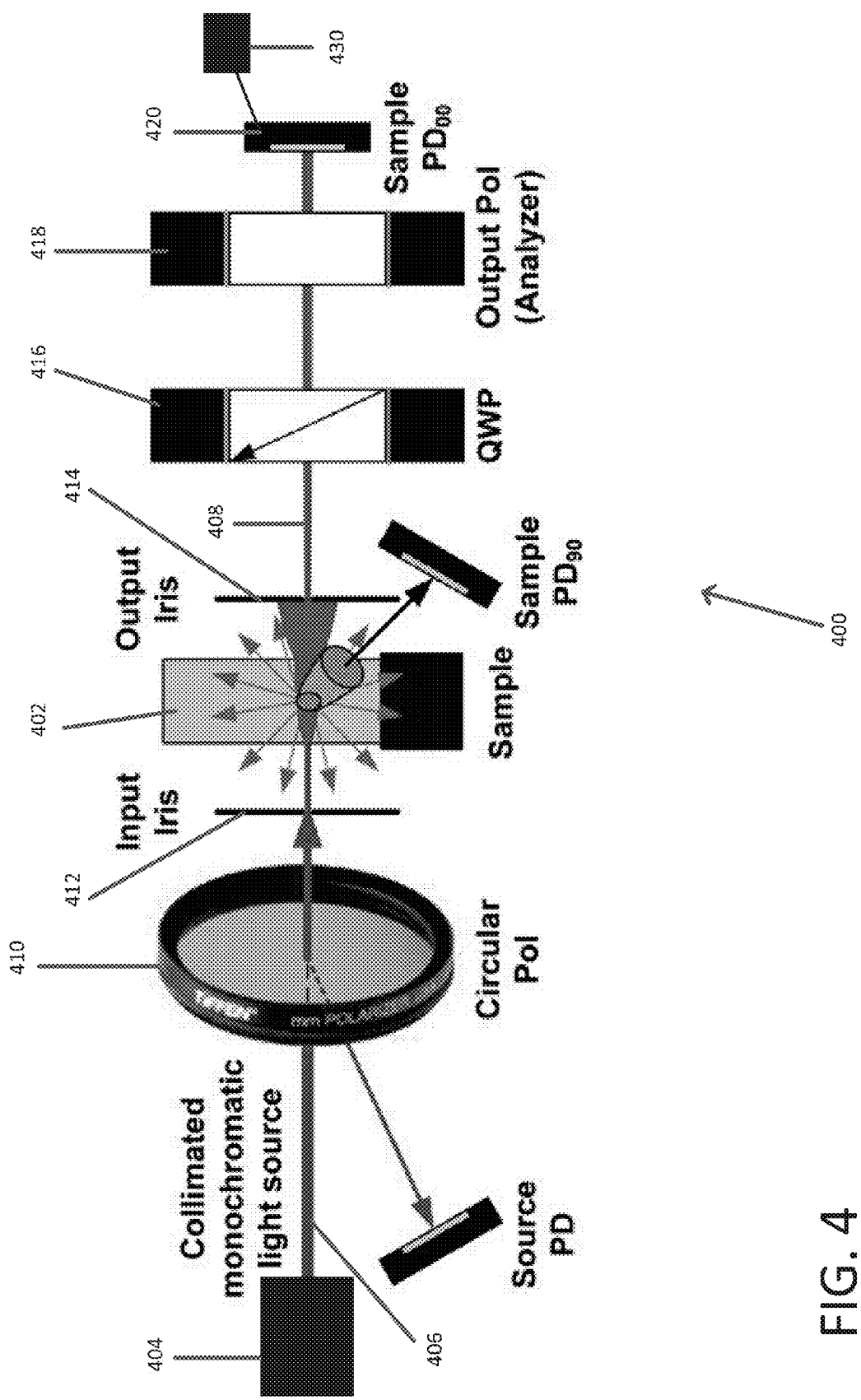
FIG. 4 shows a fourth embodiment of an optical system.

As shown in FIG. 4, a system 400 configured to assess optical properties of a sample 402 comprises an optical beam source 404 situated so as to direct an optical beam 406 along an optical axis 408. The system 400 can further comprise a circular polarizer 410, an input iris 412, an output iris 414, a quarter wave plate 416, an output polarizer 418, and a photodiode 420. In this embodiment, the circular polarizer 410 can be referred to as an input polarizer. An amplifier 430 adapted for determination of degree of polarization is coupled to the photodiode 420.

In the examples of FIGS. 1-4, at least one polarizer is situated along an optical axis between the source and the sample so that an optical beam directed to a sample has a predetermined SOP. Samples can thus modulate the SOP or other characteristics of the optical beam, and measurement of the modulated beam permits sample evaluation.

In the embodiments illustrated in FIGS. 1-3, the respective input polarizers 114, 214, 312 are linear polarizers and thus optical beams in a linear SOP of a predetermined or other known orientation referred to herein as the input plane of polarization are directed to samples. In the embodiments illustrated in FIGS. 1-3, the respective output polarizers 118, 218, 316 are situated along the respective optical axes between the samples and the photodiodes. These output polarizers are linear polarizers and can be rotated about the optical axes with respect to the respective input polarizers by a known angle of rotation, referred to herein as $\Theta$.

In the illustrated examples, an optical beam exiting a sample can have both a polarized component and an unpolarized component, depending on the optical properties of the sample. The polarized component typically has the same SOP as the beam entering the sample (linearly polarized in the input polarization plane). The unpolarized component is that portion of the optical beam scattered by the sample. The optical beam exiting the sample can be partially polarized, with a degree of polarization P, and can be represented as a sum of two components: a component attributable to the unpolarized light exiting the sample and a component attributable to the polarized light exiting the sample. Notably, the polarized light exiting the sample interacts with the output polarizer in a very different way than the unpolarized light exiting the sample does. Thus, by rotationally displacing the output polarizer with respect to the input polarizer and measuring corresponding changes to optical power measured at the photodiode, the degree of polarization of the light exiting the sample can be assessed, and optical characteristics of the sample determined based on the assessment.

In the example of FIG. 4, an optical beam is directed to a sample 402 in a circular SOP. The optical beam exiting the sample 402 can, as described above, be partially polarized and have a degree of polarization P. In the system 400, the polarized component is circularly polarized. Thus the quarter wave plate 416 is situated along the optical axis 408 between the sample 402 and the output polarizer 418 to convert the circularly polarized portion of the beam exiting the sample 402 into linearly polarized light, while leaving the unpolarized portion of the beam exiting the sample 402 unpolarized. In system 400, the output polarizer 418 can be rotationally offset about the optical axis 408 from the quarter wave plate 416 in order to facilitate measurements.

The systems 100, 200, 300, and 400 are merely illustrative. In alternative embodiments, different optical elements can be rotatable and different polarization states can be used. For example, an input polarizer can be rotated with respect to an output polarizer. Further, elliptical rather than linear polarizers can be used. In some alternative embodiments, the source of the optical beam can be an optical modulator capable of modulating the polarization of the optical beam. In such an alternative embodiment, an input polarizer may not be necessary, and an output polarizer may not need to be rotatable about the optical axis.

In other alternative embodiments, the photodetector can be capable of measuring the polarization state of light incident thereon. In such an alternative embodiment, an output polarizer may not be necessary. Further, various components are illustrated in systems 100, 200, 300, and 400, though they are not necessary. For example, though the input and output irises can help maintain consistency in the system, they are not necessary. Further, systems 100, 200, 300, and 400, as well as other suitable optical systems, can be modified such that a photodetector measures incident optical power in a reflectance geometry. For example, system 100 can be modified such that light reflected from (rather than transmitted by) the sample travels through the output iris 116, output polarizer 118, and is incident on the photodiode 120. In such an arrangement, the angle between the path of the optical beam incident on the sample and the path of the optical beam incident on the photodetector can be greater than 90° (i.e., the optical beam is reflected rather than transmitted). Similar alternative arrangements can be used with systems 200, 300, and 400, and do not change the general principles of the operation of the systems.

Once a suitable optical system (such as one of the systems 100, 200, 300, 400, described above) has been established, an optical beam can be generated at the source which propagates through the system. The appropriate optical elements of the optical system can be rotated with respect to one another while the optical beam power incident on the photodiode can be measured. If the degree of polarization P of the beam exiting the sample is 1 (that is, the beam has no unpolarized component and the sample is non-scattering) then the photodiode will provide a minimum signal when $\Theta$ is 90 degrees and a maximum signal when $\Theta$ is 0 degrees. If the degree of polarization P of the beam exiting the sample is 0 (that is, the beam has no polarized component and the sample is highly scattering) then the photodiode will give a constant signal regardless of the value of $\Theta$. When P is between 0 and 1, the photodiode will produce a signal which varies with $\Theta$, but to a lesser degree than for P=1.

Stokes vectors and Mueller matrices can be used to model the optical system 100 illustrated in FIG. 1, and the principles illustrated here are applicable generally to other embodiments of optical systems disclosed herein. The beam entering the sample 102 can be represented using the Stokes vector [1, 1, 0, 0] for completely linearly polarized light. The power associated with this Stokes vector is given the arbitrary value 1 for convenient illustration. Actual beam power can be any value so long as it is sufficient to allow the measurements described herein.

The sample 102 acts as an optical element, the effect of which can be represented by the sum of the second and third 4×4 matrices in the equation below, where the second 4×4 matrix represents preservation of the input SOP in the beam exiting the sample 102, and third 4×4 matrix represents depolarization effects on the beam exiting the sample 102. The output polarizer 118 acts as a generalized linear polarizer offset angularly from the input polarizer by angle $\Theta$, and is represented by the first 4×4 matrix, wherein $a=\cos(2\Theta)$ and $b=\sin(2\Theta)$. The first, second, and third Mueller matrices allow computation of the Stokes vector representing the beam as incident on the photodiode 120 via:

$$\frac{1}{2}\begin{bmatrix} 1+a \cdot P \\ a(1+a \cdot P) \\ b(1+a \cdot P) \\ 0 \end{bmatrix} =$$

$$\frac{1}{2}\begin{bmatrix} 1 & a & b & 0 \\ a & a^2 & a \cdot b & 0 \\ b & a \cdot b & b^2 & 0 \\ 0 & 0 & 0 & 0 \end{bmatrix} \left( \begin{bmatrix} P & 0 & 0 & 0 \\ 0 & P & 0 & 0 \\ 0 & 0 & 0 & 0 \\ 0 & 0 & 0 & 0 \end{bmatrix} + \begin{bmatrix} 1-P & 0 & 0 & 0 \\ 0 & 0 & 0 & 0 \\ 0 & 0 & 0 & 0 \\ 0 & 0 & 0 & 0 \end{bmatrix} \right) \cdot \begin{bmatrix} 1 \\ 1 \\ 0 \\ 0 \end{bmatrix}$$

Thus, the power measured by the photodiode 120 is $\frac{1}{2}(1+a*P)$, which is equivalent to $\frac{1}{2}(1-P)+P*\cos^2(\Theta)$. This second expression is useful because the first term represents the component of the measured intensity attributable to the unpolarized light exiting the sample 102 and the second term represents the component of the measured intensity attributable to the polarized light exiting the sample 102. Power measurements at one or more angles can thus permit determination of the degree of polarization P.

In the discussion above, the power of the optical beam incident on the sample was given the arbitrary value 1, and it was noted that this intensity could in fact be any of a wide range of intensities. To allow quantitative evaluation of P, a calibration procedure is executed based on a maximum power measurable for the system (i.e., the particular source, polarizers, ambient light conditions, etc.) by the photodiode. This can be accomplished by first offsetting the measured power to eliminate any effects of optical system imperfections, thereby calibrating the system. An optical power at the detector is measured with a non-scattering sample or without a sample for which P=1. The analyzer is set to substantially block an input SOP to obtain a minimum received power. If the minimum value does not correspond to zero, an offset is introduced until the result is about zero. For a linear polarizer/analyzer combination, this measurement is accomplished by setting $\Theta=90°$. A maximum measurable power is obtained by setting $\Theta=0°$. This power is referred to as $I_{max}$, and allows quantitative evaluation of other samples by measuring the power at the photodetector ($I_{measured}$) in the calibrated system and determining P via:

$$I_{measured}=I_{max}*[½*(1-P)+P*\cos^2(\Theta)]=I_{max}*[½*(1+P*\cos(2\Theta))].$$

Thus, in one example, if $I_{measured}=½*I_{max}$ for $\Theta=37°$, then P can be determined to be zero (i.e., the beam exiting the sample has no polarized component). As another example, if $I_{measured}=0.375*I_{max}$ for $\Theta=60°$, then P can be determined to be 0.50.

Figure 5:
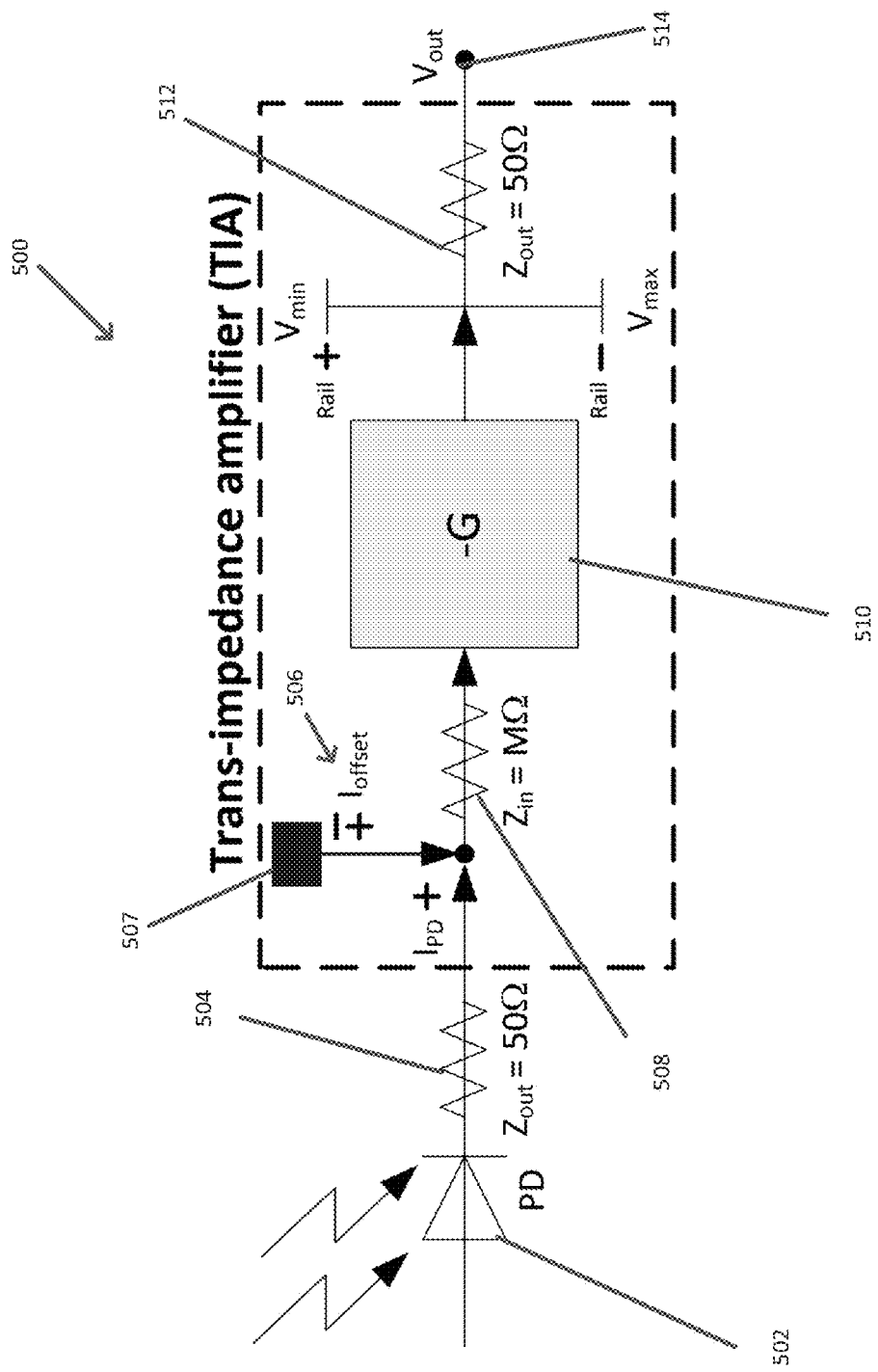
FIG. 5 illustrates a representative photosignal processing circuit.

The photosignal (typically photocurrent) produced by a photodiode can be coupled to an amplifier or other processing circuitry to facilitate determination of P. FIG. 5 illustrates a convenient representation of a processing circuit 500, but in typical examples, processing is based on one or more differential amplifiers. As illustrated in FIG. 5, a photodiode 502 is coupled to direct a photocurrent to a resistor 504. In one example, the resistor 504 is a 50Ω resistor, but different values can be used. The current can then be offset using an offset current 506 provided by an offset current source 507. The combined photocurrent and offset current are coupled to a second resistor 508 to produce a corresponding signal voltage. In a specific example, the second resistor 508 can be a 1 MΩ resistor, but other values can be used. An amplifier 510 provides a gain G to the signal voltage, and an output voltage is coupled to an output resistor 512, shown in FIG. 5 as a 50Ω resistor. Other values can be used. The voltage resulting at node 514 can be read into a signal capture system, processed by an ADC, or be directed to other devices and/or be recorded for later analysis as desired. This voltage is referred to herein as the output voltage.

Various components of the processing circuit 500 can be variable, allowing further conditioning of the current produced by the photodiode prior to reading of the output voltage. For example, in the illustrated embodiment, the offset current 506 and the gain 510 can be variable, thus allowing the output voltage read from node 514 to be scaled and/or offset as desired. In one exemplary embodiment, the output voltage can be run through an analog to digital converter, and then fed into a digital computing device such as a personal computer. In such an embodiment, the computer can be used to display the measured voltages on a display device, print voltage data to a printer, and/or save voltage data to any of various suitable data storage devices.

A relationship between the maximum current produced by the photodiode ($i_0$), P, $\Theta$, offset current ($I_{offset}$), gain (G), impedance ($Z_{out}$), and the output voltage ($V_{out}$) can be derived based on the characteristics of the optical system (i.e., using the output Stokes vector derived above) and the electric circuit:

$$\frac{i_0}{2}[1+P\cdot\cos(2\theta)] = I_{offset} - \frac{V_{out}}{G\cdot Z_{out}}$$

The offset current, gain, impedance, and $\Theta$ are selected as desired and the output voltage is measured based on the selected values. The system can be calibrated and $i_0$ can be determined using a completely non-scattering sample (or no sample) for which P=1, as described above with regard to the determination of $I_{max}$. Thus, the degree of polarization of the beam exiting a sample can be determined.

In some embodiments, exemplary systems can be configured to facilitate what is referred to herein as a zero-crossing analysis. For example, a load attenuator can be used to first attenuate the current produced by the photodiode. This attenuation of the current helps to ensure that the current offset (which in some cases can be limited to a narrow range) can be used so that an offset, attenuated current, when plotted on a curve against $\Theta$, crosses zero for some value of $\Theta$. A large gain can then be applied in order to increase the sensitivity of the measurements. As the gain increases in such a system, power measurements, when plotted against $\Theta$, appear closer and closer to a step function, where the step occurs at the angle $\Theta$ for which the measured intensity is zero and the size of the step is defined by the capabilities of the system. While zero crossings can be convenient, in other examples, other crossing values can be used between a maximum and a minimum amplifier output value. For example, values of 0.1, 0.2, 0.5, and 0.75 of a maximum or minimum value can be used.

In some embodiments, exemplary systems can be tuned by providing a non-scattering sample (or no sample), for which P can be 1, and adjusting the offset current until the zero crossing approaches $\Theta=90°$. Once the system has been tuned in this way, various scattering samples can be placed in the system and evaluated to determine the $\Theta$ at which the zero crossing occurs, referred to herein as $\Theta_c$. Based on the systems described and the analysis presented above, a well-defined relationship exists and allows the computation of P from $\Theta_c$:

$$i_0\cdot[1+P\cdot\cos(2\Theta_c)]=2\cdot I_{offset}$$

This can provide a convenient method for determining P: rotating the output polarizer until a zero voltage reading is obtained, then calculating P using the above equation. This technique can be particularly advantageous because it can allow for a very large gain to be utilized, which can provide increased sensitivity of the system, especially when the intensity of the light beam incident on the photodetector is relatively low. In tests, transimpedance gains G of up to $10^7$ have been used. As used herein, transimpedance gain can be referred to without units or in units of Ohms, as may be convenient.

Figure 6:
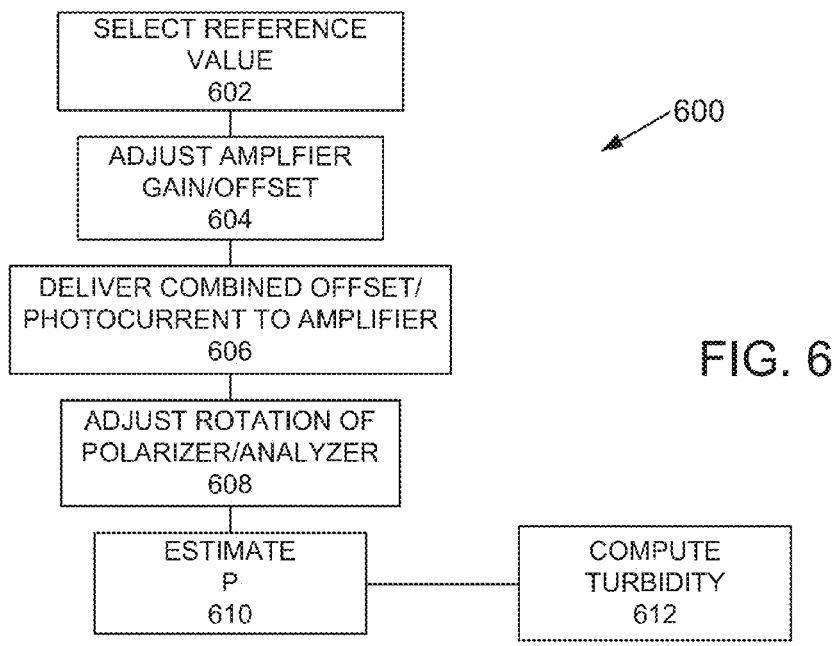
FIG. 6 is a block diagram of a representative method of estimating turbidity.

In a representative method 600 shown in FIG. 6, at 602, a reference value is selected. Typically, a reference value of zero is selected for measurements based on so-called zero crossings. At 604, an input offset and signal gain are selected. The input offset is typically a current offset, and gain is selected so that an amplifier output is saturated at minimum and maximum values associated with amplifier power supply voltages for input photocurrents that differ from the offset current by less than 10%, 5%, 1%, 0.5%, or 0.1%. In some examples, an input photocurrent is attenuated, and the attenuated photocurrent and offset current are combined for delivery to the amplifier at 606. At 608, an angle of rotation between a polarizer and analyzer situated to analyze an optical beam directed to and from a sample is varied so as to produce an amplifier output associated with the reference value. A degree of polarization is estimated at 610 based on the angle of rotation, and at 612, a turbidity value associated with the sample is computed. While the method 600 can be accomplished with analog amplification and signal processing, digitized currents and reference values can be used so that offsets and gains are based on stored digital values. In some examples, such processing is based on combined digital and analog representations.

Figure 7:
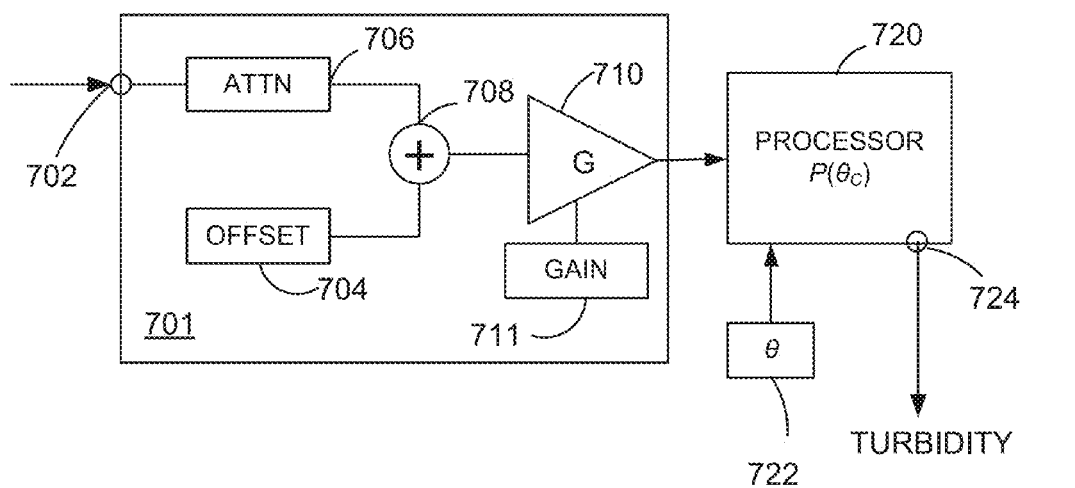
FIG. 7 is a schematic diagram of a representative photosignal processing system configured to determine sample turbidity based on a polarizer/analyzer angle of rotation associated with a zero-crossing.

Referring to FIG. 7, a photosignal processing system 700 includes a photosignal amplifier 701 having an input 702 coupled to receive a photosignal such as a photocurrent or photovoltage. An attenuator 706 is situated to attenuate the photosignal (typically a photocurrent), and couple the attenuated photosignal to a summing junction 708. An offset generator 704 is situated to couple an offset (typically an offset current) to the summing junction 708. The summed photosignal and offset are coupled to an amplifier 710 having a gain G established based on a gain control 711. The amplifier 710 is coupled to a signal processor 720 that determines a degree of polarization based on an angle associated with a zero-crossing (or crossing of another reference value). In some examples, a polarizer/analyzer angle of rotation is coupled to the signal processor 720 via an encoder 722. In some cases, the encoder signal is converted into an angle of rotation by the signal processor 720. Upon determination of the zero-crossing angle and associated degree of polarization, the signal processor 720 can also determine a turbidity and report or display an associated value via an output 724.

In some embodiments, correction for various systemic errors can also be accomplished. For example, errors due to slight depolarization of light entering a sample (due, e.g., to defects and multiple reflections in optical components), photonic noise in a photodetector, electronic noise in electrical circuits, and noise in any analog to digital signal converter can be determined using a sample having predictable optical properties (e.g., air). Various adjustments to components of the system can be made to correct for these errors (e.g., so that measurements match expectations based on the predictable properties of the sample). As another example, errors due to the presence of a sample container (e.g., a cylindrical container which can have an optical effect on the optical beam) can be determined using a sample having predictable optical properties (e.g., de-ionized water). Again, various adjustments to components of the system can be made to correct for such errors (e.g., so that measurements match expectations based on the predictable properties of the sample).

As one example of an error correction procedure, $\Theta_c$ can be measured for de-ionized water, for which $\Theta_c$ is expected to be 90°, and can be referred to as $\Theta_{cDI}$. Thereafter, measurements of $\Theta_c$ for other samples can be corrected using $\Theta_{cDI}$. Because the rate of change of P varies non-linearly with $\Theta_c$, the value of the gradient at each experimentally determined value has to be accounted for when implementing systemic error correction. For example, the rate of change of P with respect to $\Theta_c$, referred to herein as $\dot{P}$, can be used to determine a corrected value of $\Theta_c$ via:

$$\theta_{c_{cor}} = \left(\frac{90 - \theta_{c_{DI}}}{\dot{P}|_{\theta_{c_{DI}}}}\right) \cdot \dot{P}\bigg|_{\theta_c} + \theta_c$$

Thus far, systems, devices, and methods have been described which allow the determination of P, the degree of polarization of light exiting a sample. Because the polarization state of the light entering the sample is generally known and well-defined (in system 100, for example, the light entering the sample 102 is completely linearly polarized), the degree of polarization of the light exiting the sample can be determined. Degree of polarization of light exiting the sample can be, in and of itself, a useful measurement. It can also additionally be correlated with other properties of scattering samples, such as concentrations of suspended solids, turbidity, haze, etc. In some cases, such relationships may be known a priori, and measurements of P made using the systems, devices, or methods described herein can be converted to values of turbidity or concentration based on those relationships. In other cases, those relationships can be determined empirically using the methods, systems, and devices described herein with samples having known values for the other properties, such as known concentrations or turbidities. In such cases, once the relationship between P and the other property has been reliably determined, samples of unknown values for the other property can be tested to determine P, which can be converted to a value for that other property via the empirically determined relationship.

In one specific embodiment combining several of the features previously described, a 4 mW, 635 nm collimated laser light source (Power Technologies, Inc., AR) is used. The optical beam produced passes through a 52 mm circular polarizer (Teffen, Japan), a circular iris aperture, a horizontal polarizer (Thorlabs, Newton, N.J.), a sample contained in a 12 mL, 19×68 mm soda-lime glass cylindrical sample vial, a second circular iris aperture, and a Glan Thompson polarizer mounted in a motorized angle stage (Altos Photonics, Inc., Bozeman, Mont.). Finally, the optical beam impinges on an adjustable transimpedance gain photodiode (PDA55, Thorlabs, Newton, N.J.). The beam power incident on the photodiode are converted to voltage signals and conditioned and additionally amplified using a variable gain broadband transimpedance amplifier (Wide-Bandwidth Amplifier, WBA; CVI Melles Griot, Albuquerque, N.M.). The voltage output is then converted to a digital input by an analog-to-digital converter and recorded by a computer. A custom LabVIEW® (National Instruments Corp., Austin, Tex.) program is executed to set analyzer polarization angle, acquire, and save data.

Such an experimental setup was built and used to analyze samples of various concentrations of nondairy creamer mixed with water. Results of these tests are presented in Table 1, in which C is the concentration of the nondairy creamer in the water and P is the degree of polarization of light leaving the sample. Raw denotes uncorrected data, Cor denotes corrected data, and Δ denotes the difference between the two. $\dot{P}|_{\Theta_c}$ represents the value of $\dot{P}$ evaluated at the raw critical angle.

TABLE 1

| C (g/ml) × | $\Theta_c$ | | | P | | | |
|---|---|---|---|---|---|---|---|
| $10^{-3}$ | Raw | Cor | Δ | Raw | Cor | Δ | $\dot{P}|_{\Theta_c}$ |
| 1.5556 | 12.059 | 13.796 | 1.737 | 0.3412 | 0.3444 | 0.0031 | 0.0963 |
| 1.4519 | 39.858 | 47.336 | 7.478 | 0.4553 | 0.5175 | 0.0622 | 0.4146 |
| 1.3551 | 46.713 | 56.277 | 9.564 | 0.5114 | 0.6149 | 0.1035 | 0.5303 |

TABLE 1-continued

| C (g/ml) × $10^{-3}$ | $\Theta_c$ | | | P | | | $\dot{P}|_{\Theta_c}$ |
|---|---|---|---|---|---|---|---|
| | Raw | Cor | Δ | Raw | Cor | Δ | |
| 1.2647 | 50.730 | 61.624 | 10.894 | 0.5485 | 0.6831 | 0.1345 | 0.6041 |
| 1.1804 | 54.427 | 66.566 | 12.139 | 0.5919 | 0.7563 | 0.1644 | 0.6731 |
| 1.1017 | 57.746 | 70.960 | 13.214 | 0.6336 | 0.8223 | 0.1887 | 0.7328 |
| 1.0283 | 60.076 | 73.980 | 13.904 | 0.6632 | 0.8655 | 0.2023 | 0.7710 |
| 0.9597 | 61.708 | 76.040 | 14.333 | 0.6871 | 0.8945 | 0.2074 | 0.7948 |
| 0.8957 | 63.505 | 78.240 | 14.735 | 0.7130 | 0.9225 | 0.2095 | 0.8171 |
| 0.7803 | 66.067 | 81.207 | 15.140 | 0.7502 | 0.9549 | 0.2046 | 0.8396 |
| 0.0000 | 76.912 | 90.000 | 13.088 | 0.9056 | 1.0000 | 0.0944 | 0.7258 |

Figure 8:
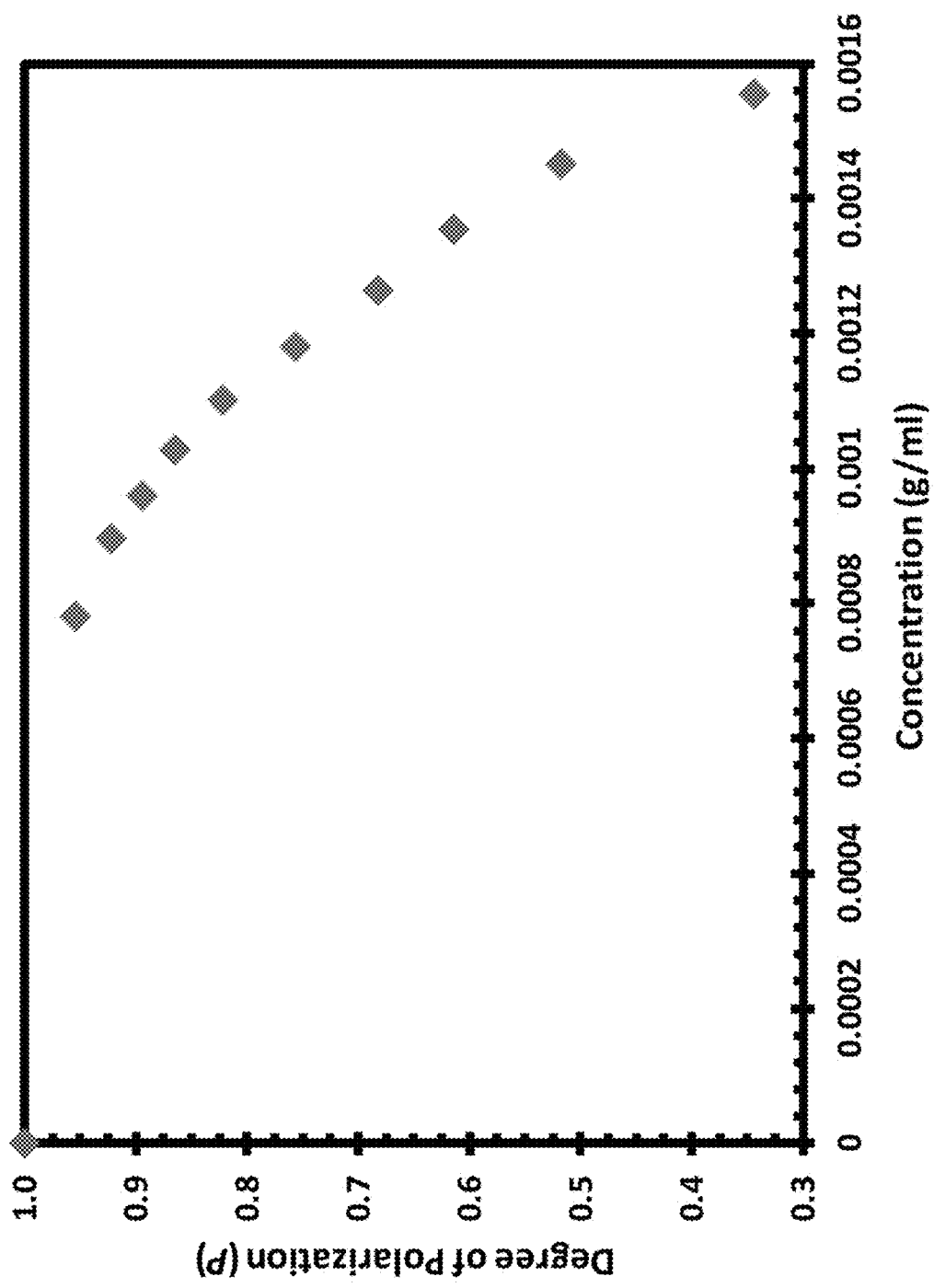
FIG. 8 shows experimental results of tests conducted using nondairy creamer.

FIG. 8 illustrates the corrected values of P shown in Table 1 plotted against the corresponding concentrations, illustrating a well-defined curve indicating a relationship between the concentration of the nondairy creamer and P. By assuming the existence of a relationship between P and C wherein C is proportional to the square root of the arccosine of P (in radians), and determining a best fit line with a processor, the following relationship (with $R^2$=0.9995) was determined:

$$\mathrm{sqrt}(a\cos(P))=707.08*C-0.0001$$

Figure 9:
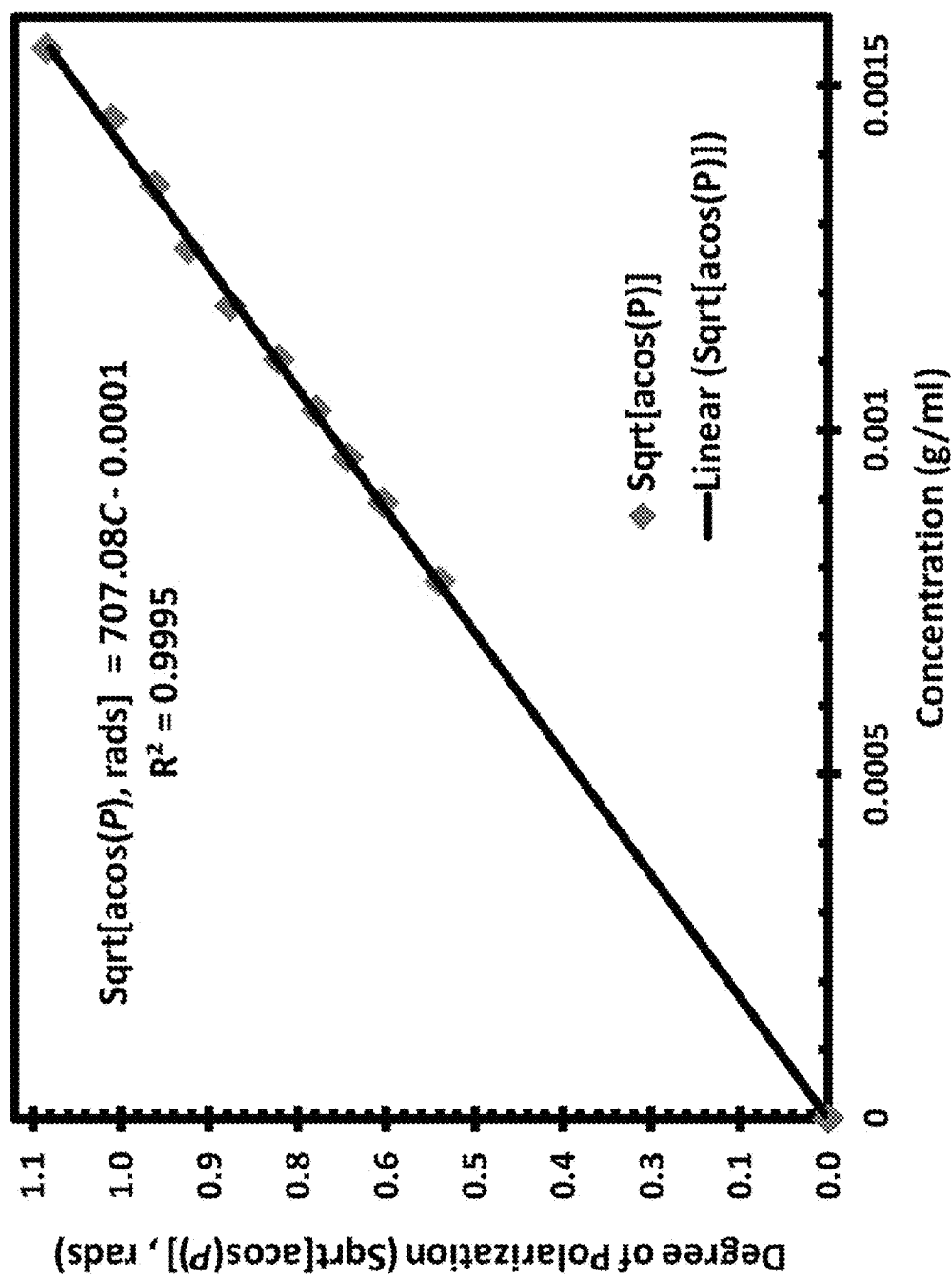
FIG. 9 shows a best fit line generated based on the experimental results of FIG. 8.
Figure 10:
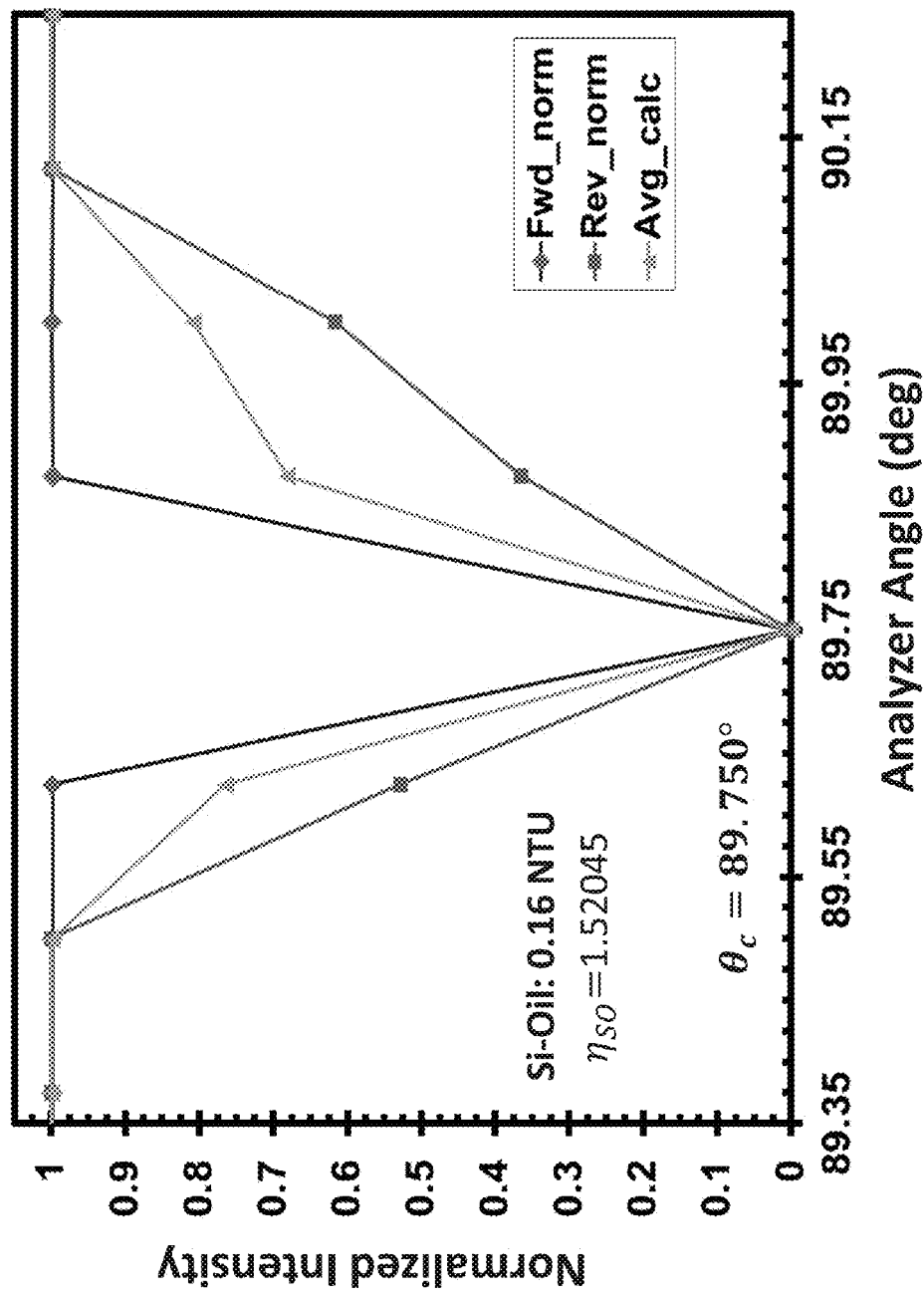
FIG. 10 shows experimental results of tests conducted using silicone oil.

FIG. 9 illustrates this relationship. The experiment was run four times for each concentration of the nondairy creamer, with results of the several runs, including mean values and standard deviations, presented in Table 2:

TABLE 2

| C (g/ml) × $10^{-3}$ | P | | | | |
|---|---|---|---|---|---|
| | μ | σ | Model | Δ | % Error |
| 1.5556 | 0.3444 | 0.0067 | 0.3534 | -0.0091 | 2.63 |
| 1.4519 | 0.5175 | 0.0051 | 0.4944 | 0.0231 | 4.46 |
| 1.3551 | 0.6149 | 0.0044 | 0.6075 | 0.0074 | 1.20 |
| 1.2647 | 0.6831 | 0.0042 | 0.6970 | -0.0140 | 2.05 |
| 1.1804 | 0.7563 | 0.0027 | 0.7671 | -0.0108 | 1.43 |
| 1.1017 | 0.8223 | 0.0018 | 0.8215 | 0.0008 | 0.09 |
| 1.0283 | 0.8655 | 0.0016 | 0.8636 | 0.0019 | 0.22 |
| 0.9597 | 0.8945 | 0.0009 | 0.8959 | -0.0014 | 0.16 |
| 0.8957 | 0.9225 | 0.0016 | 0.9207 | 0.0018 | 0.20 |
| 0.7803 | 0.9549 | 0.0011 | 0.9541 | 0.0008 | 0.08 |
| 0.0000 | 1.0000 | 0.0000 | 1.0000 | 0.0000 | 0.00 |

As shown in Table 2, the standard deviation of the measurements generally increased as concentration increased, reaching a maximum of 0.0067.

Figure 11:
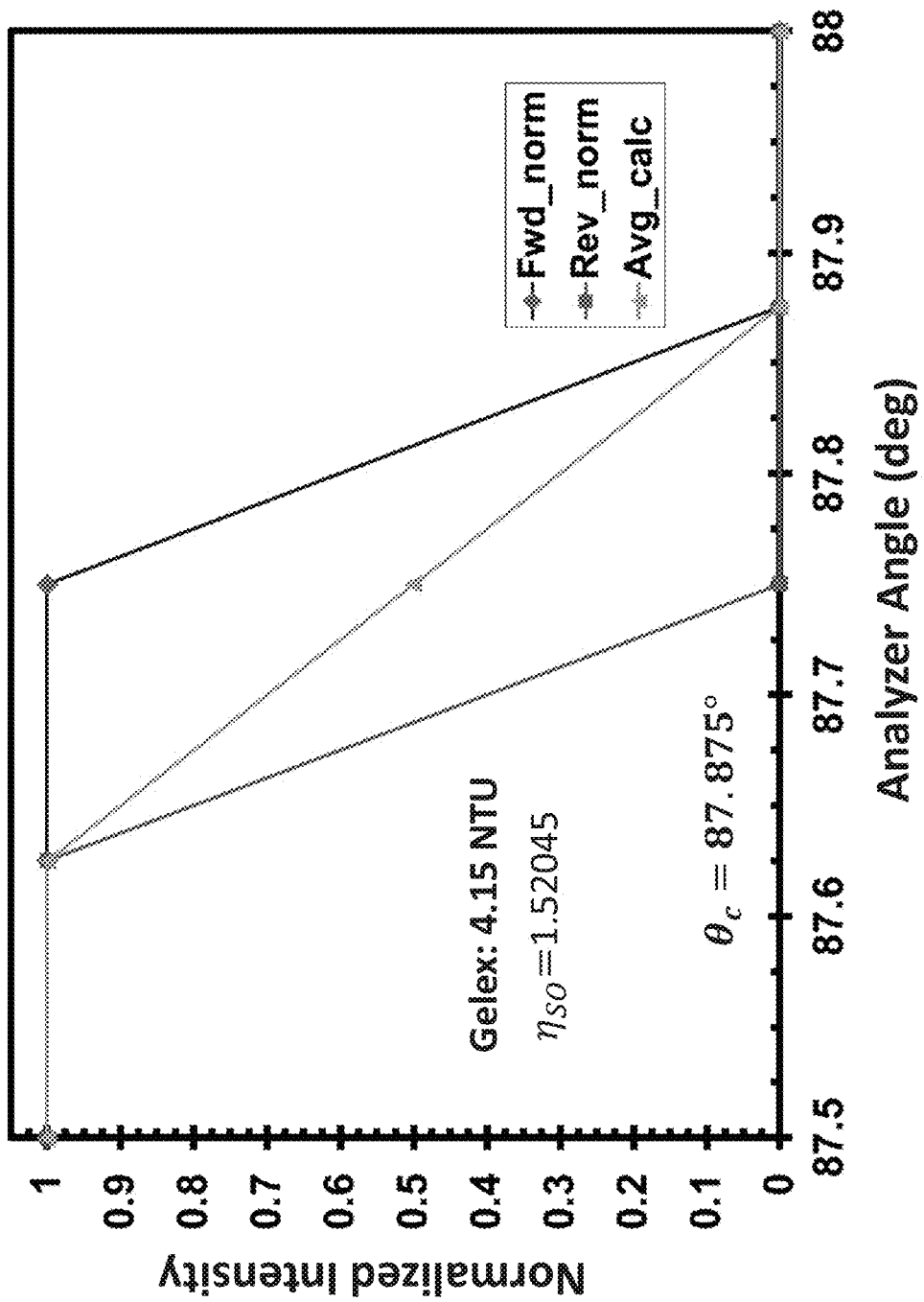
FIG. 11 shows experimental results of tests conducted using Gelex having 4.15 NTU.
Figure 12:
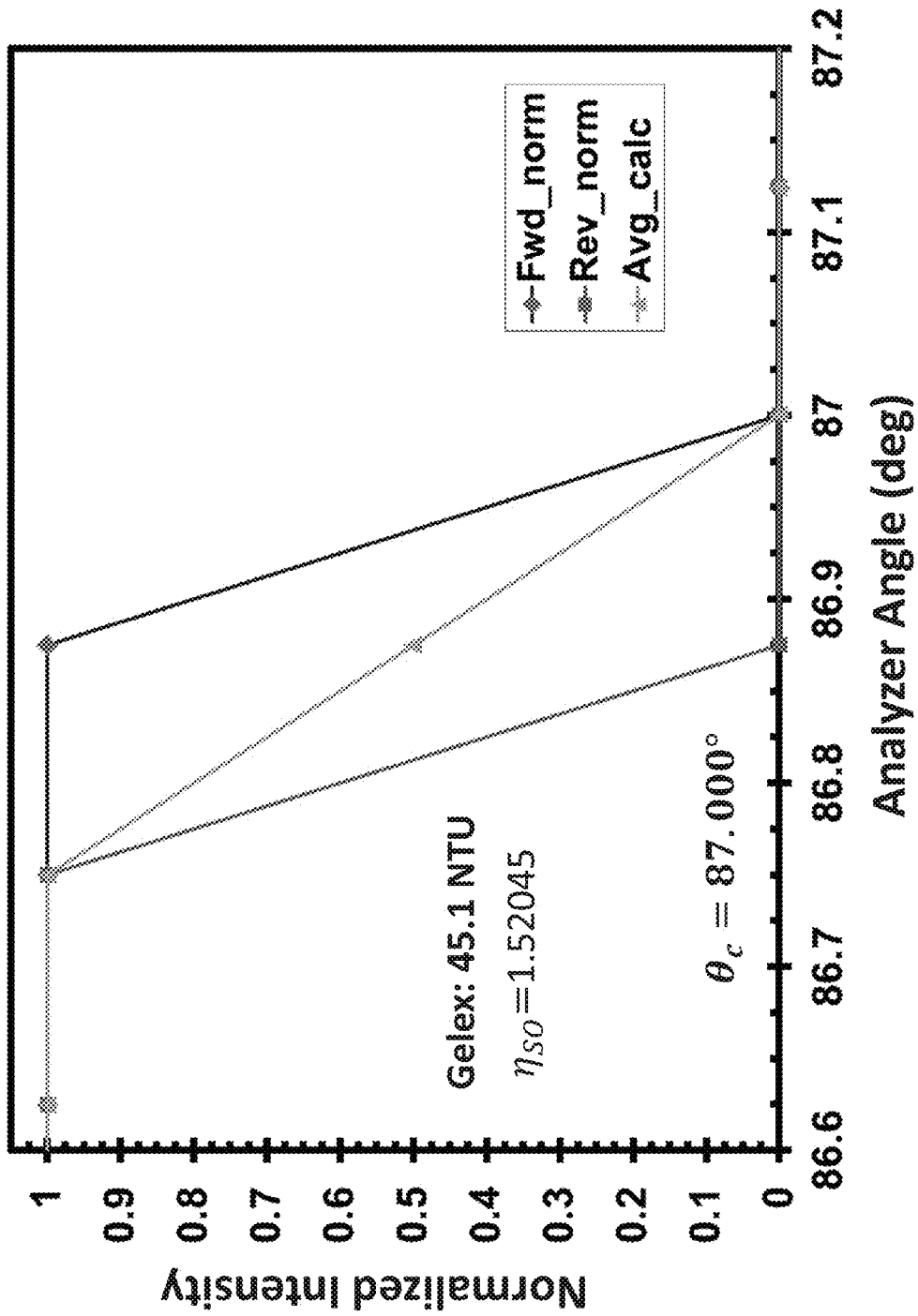
FIG. 12 shows experimental results of tests conducted using Gelex having 45.1 NTU.
Figure 13:
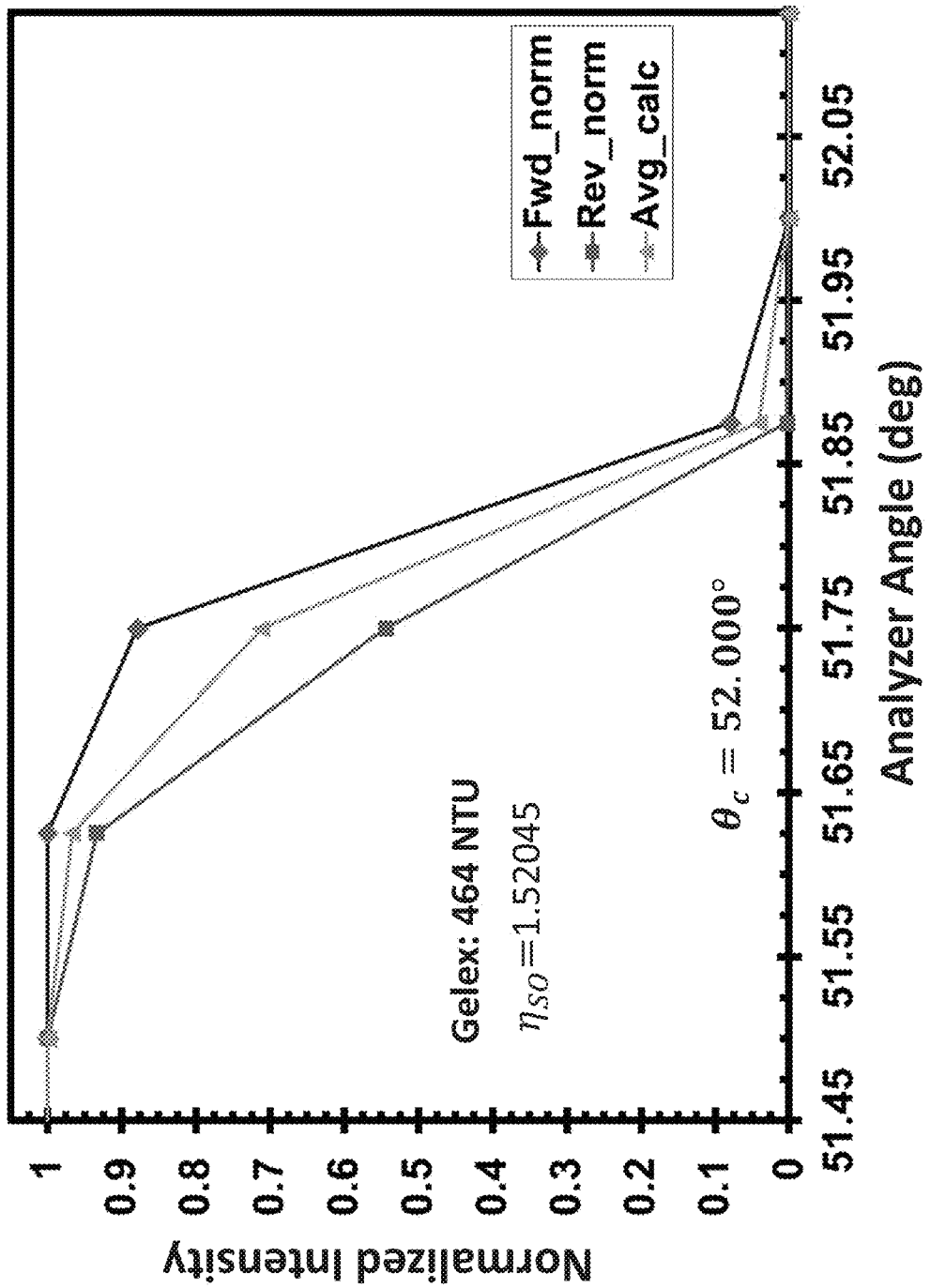
FIG. 13 shows experimental results of tests conducted using Gelex having 464 NTU.

FIGS. 10-13 show results from several other experiments using the same equipment described above. For each experiment, measurements were taken twice, once by rotating the output polarizer in each direction. The results shown in FIGS. 10-13 illustrate data from both trials for each experiment, as well as an average of the two. The results shown in FIGS. 10-13 also represent normalized intensities—the measured intensities offset and scaled such that the maximum intensity was 1.0 and the minimum intensity was 0.0. In the first case, (FIG. 10) silicone oil (having refractive index 1.52045 and 0.16 nephelometric turbidity units (NTU)) in a 19 mm diameter soda-lime Pyrex vial (having refractive index 1.51454) was used to calibrate the system. The load attenuator (Kay Elemetrics Corp.) was set to 15 dB, the gain to $10^7$, and the current offset was adjusted until $\Theta_c$ was determined to be 89.75° (representing a 0.25° systemic error). FIGS. 11-13 show results from subsequent experiments in which the samples comprised Gelex having 4.15, 45.1, and 464 NTU, respectively. As shown, for Gelex having 4.15 NTU, $\Theta_c$ was measured to be 87.875°, for Gelex having 45.1 NTU, $\Theta_c$ was measured to be 87.000°, and for Gelex having 464 NTU, $\Theta_c$ was measured to be 52.000°.

In view of the many possible embodiments to which the principles of the disclosed invention may be applied, it should be recognized that the illustrated embodiments are only preferred examples of the invention and should not be taken as limiting the scope of the invention. Rather, the scope of the invention is defined by the following claims. I therefore claim as my invention all that comes within the scope and spirit of these claims.

I claim:

1. An optical system for inspecting a sample, comprising:
   an input polarizer situated to receive an optical beam, produce a polarized input optical beam, and direct the polarized input beam to the sample;
   an output polarizer situated to receive the polarized input optical beam from the sample and form an output optical beam;
   a photodetector situated to receive the output optical beam; and
   a photodetector processor coupled to the photodetector and configured to provide an output value based on a comparison of a photosignal from the photodetector and a predetermined reference value, wherein the photosignal from the photodetector is a photocurrent, the photodetector processor is configured to combine an offset current with the photocurrent to form an output current, the reference value is associated with the output current, and wherein the output value is associated with a degree of polarization of the output optical beam.

2. The optical system of claim 1, wherein the photodetector processor is configured to indicate a photosignal transition about the reference value based on a rotation of the output polarizer.

3. The optical system of claim 1, wherein the photodetector processor is configured so that the reference value is a zero value.

4. The optical system of claim 3, wherein the photodetector processor is configured to provide an estimate of a degree of polarization based on an output polarizer angle of rotation.

5. The optical system of claim 4, wherein the photodetector processor is configured to indicate a zero crossing.

6. The optical system of claim 5, wherein the input polarizer and the output polarizer are linear polarizers.

7. The optical system of claim 5, wherein the input polarizer and the output polarizer are circular polarizers.

8. The optical system of claim 1, wherein the photodetector processor is configured such that the output transitions from a minimum value to a maximum value at output polarizer rotation angles within 1.0 degree of the rotation angle associated with the reference value.

9. The optical system of claim 8, wherein the reference value is midway between values associated with maximum and minimum optical intensity.

10. The optical system of claim 1, wherein the output value provided by the photodetector processor is adapted to transition between a maximum output value and a minimum output value at a photocurrent magnitude corresponding to the reference value.

11. The optical system of claim 10, wherein the photodetector processor establishes the degree of polarization based on an orientation of the output polarizer that is associated with a photocurrent magnitude corresponding to the reference value.

12. The optical system of claim 10, wherein the minimum value is a negative value and the maximum value is a positive value, wherein the minimum and maximum values are associated with a photodetector processor power supply.

13. The optical system of claim 1, wherein the photodetector processor is configured to estimate a sample turbidity based on the degree of polarization associated with the output value.

14. The optical system of claim 1, further comprising a source configured to provide the optical beam.

\* \* \* \* \*